United States Patent [19]
Hoegnelid et al.

[11] Patent Number: 5,433,731
[45] Date of Patent: Jul. 18, 1995

[54] MECHANICAL DEFIBRILLATOR AND METHOD FOR DEFIBRILLATING A HEART

[75] Inventors: Kurt Hoegnelid, Voesterhuninge; Liliane Wecke, Sundbyberg; Kenth-Ake-Sune Nilsson, Akersberga; Jan Ljungstroem, Solna, all of Sweden

[73] Assignee: Pacesetter AB, Solna, Sweden

[21] Appl. No.: 210,467

[22] Filed: Mar. 21, 1994

[30] Foreign Application Priority Data

Mar. 29, 1993 [SE] Sweden .................... 9301055

[51] Int. Cl.$^6$ .................................... A61N 1/39
[52] U.S. Cl. ............................ 607/5; 601/48; 601/148; 600/16
[58] Field of Search ............ 600/16, 17; 601/48, 601/108, 148–153; 607/5

[56] References Cited

U.S. PATENT DOCUMENTS

| | | | |
|---|---|---|---|
| 750,735 | 1/1904 | Turck | 601/108 X |
| 3,587,567 | 6/1971 | Schiff | 601/153 X |
| 3,857,382 | 12/1974 | Williams, Jr. et al. | 600/17 |
| 4,265,228 | 5/1981 | Zoll | 601/108 |
| 4,621,617 | 11/1986 | Sharma | 600/16 |
| 4,925,443 | 5/1990 | Heilman et al. | 600/16 |
| 4,957,477 | 9/1990 | Lundbäck | 600/16 |
| 5,098,369 | 3/1992 | Heilman et al. | 600/16 |

FOREIGN PATENT DOCUMENTS 0429141 5/1991 European Pat. Off. .

OTHER PUBLICATIONS

Current Problems in Cardiology, vol. XIV, No. 12, Dec. 1989, p. 699.

*Primary Examiner*—Lee S. Cohen
*Assistant Examiner*—Jeffrey R. Jastrzab
*Attorney, Agent, or Firm*—Hill, Steadman & Simpson

[57] ABSTRACT

An implantable heart defibrillator and a method for defibrillating a heart, employ a shock pulse generator for delivering a defibrillation shock to a heart, the delivered energy being mechanical. The shock pulse generator includes an electromechanical energy converter which generates, e.g., pressure, by means of a piezoelement, in a pressure chamber. Pressure is transmitted by a fluid in an electrode devised like a hydraulic line to a balloon-like electrode head in contact with heart tissue. The generated pressure causes the electrode head to expand and deliver a mechanical shock to the heart corresponding to the pressure.

34 Claims, 5 Drawing Sheets

MECHANICAL DEFIBRILLATOR AND METHOD FOR DEFIBRILLATING A HEART

BACKGROUND OF THE INVENTION

1. Field of the Invention

The present invention relates generally to an implantable heart defibrillator of the type including means for sensing the occurrence of fibrillation and for emitting at least one defibrillation shock in response, and to a method for defibrillating a heart.

2. Description of the Prior Art

A modern automatic, implantable defibrillator, e.g. as described in Current Problems in Cardiology, Volume XIV, No. 12, Dec. 1989, Chicago, Troup J. P. "Implantable Cardioverters and Defibrillators", p. 699 ff, especially FIG. 14 and its legend, includes cardioversion and pacemaker stimulation capability for both tachycardia and bradycardia, in addition to a defibrillation function, and is sometime referred to as an AICD (automatic implantable cardioverter defibrillator). In AICD defibrillation, an attempt is made to induce all heart cells to depolarize simultaneously by imposing a strong electrical field across the heart, i.e. the heart is electrically shocked. The electrical shock takes the form of electrical pulses which can sometimes be emitted in patterns of varying spatial and temporal sophistication.

Achieving depolarization of heart cells by mechanically touching them is also known. The result is a heartbeat achieved mechanically. One possible explanation of this phenomenon is that mechanical contact causes leakage from the cellular ion channels. A change then occurs in ion concentrations inside and outside the cell membrane, thereby triggering alepolarization and thus a heartbeat.

This knowledge regarding mechanical depolarization has, however, not been employed in the art of defibrillation which, with the exception of devices for injecting fibrillation-terminating drugs into the heart, (e.g., European Application 0 429 141), has concentrated exclusively on defibrillation by electrical shock. Considerable electrical energy (about 5–40 J) is required for defibrillation. Tissue subjected to such energy in the form of an electrical shock could be damaged. For this reason, efforts are being undertaken in the art in an attempt to reduce the electrical energy needed for defibrillation.

One procedure for achieving this reduction mechanically is described in U.S. Pat. No. 4,925,443, which relates to an artificial, implantable mechanical support function for ventricular compression of the heart. However, any defibrillation necessary in the patient is still performed electrically. The mechanical support function is used in conjunction with de,fibrillation only to compress the heart so a lower level of electrical defibrillation energy can be used.

SUMMARY OF THE INVENTION

An object of the present invention is to provide a system and method to terminate a fibrillation condition in the heart by supplying the heart with a non-electrical shock instead of an electrical shock.

The above object is achieved in accordance with the principles of the present invention in an implantable defibrillator which includes a shockwave generator that delivers at least one shockwave to the heart, the shockwave containing non-electrical, e.g., mechanical, energy. The shockwave generator includes an energy converter (transducer) for converting electrical energy into the mechanical energy to be delivered to the heart. In various embodiments, the electrical-to-mechanical conversion may be accomplished piezoelectrically, electromagnetically, electrochemically, electrostrictively, magnetostrictively, or by means of bubble jet generation.

In the method of the invention, the above object is achieved by converting electrical energy into some other form of energy (non-electrical energy), and delivering at least one shockwave containing the non-electrical energy to the heart, to defibrillate the heart. The step of converting the electrical energy into some other form of energy is preferably accomplished by converting the electrical energy into mechanical energy. The step of converting the electrical energy into mechanical energy may be accomplished by transducing the electrical energy piezoelectrically, electromagnetically, or electrochemically, in various embodiments.

In accordance with the invention, the mechanical energy in the defibrillation shock induces one or more mechanical shockwaves in the heart, thereby subjecting the heart cells to a simultaneous depolarization, which is equivalent to a defibrillation.

DESCRIPTION OF THE PREFERRED EMBODIMENTS

Figure 1:
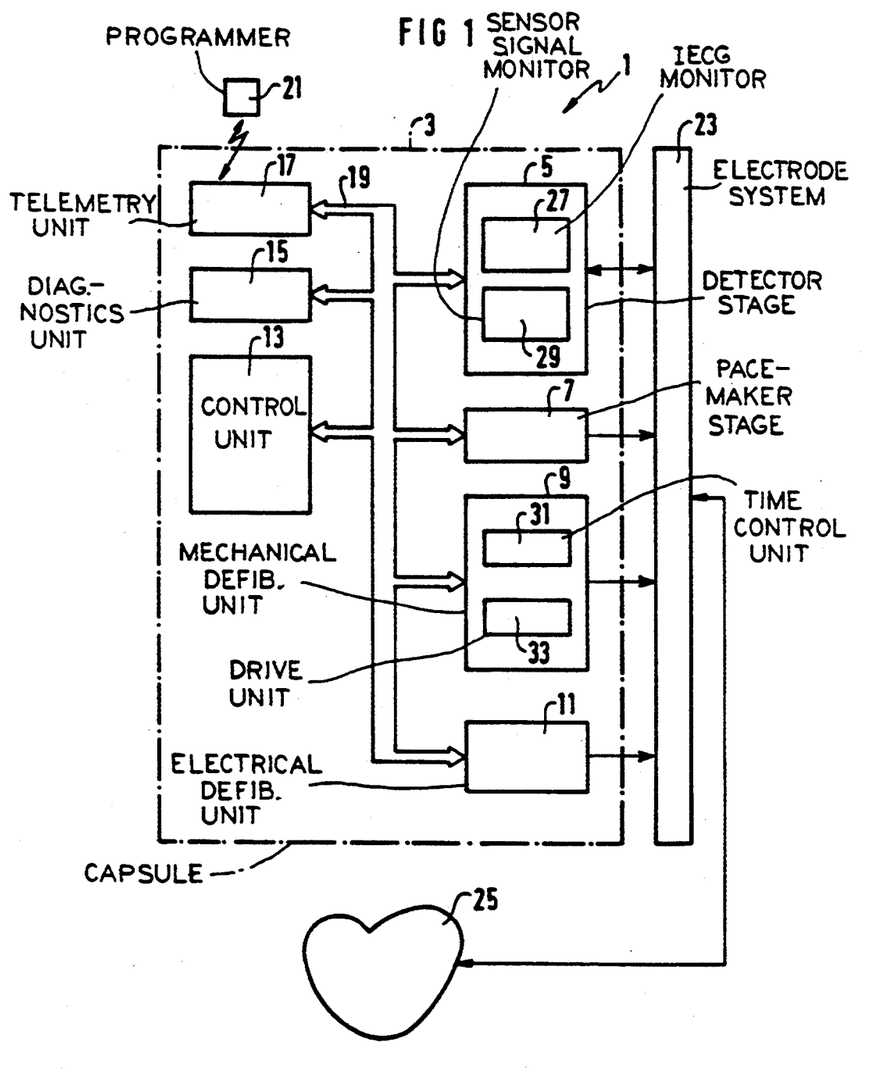
FIG. 1 is a block diagram of a defibrillation system constructed in accordance with the principles of the present invention.

The block diagram in FIG. 1 shows an example of a defibrillator system according to the invention. The system of FIG. 1 includes a defibrillator implant 1 whose enclosure can consist of, e.g., a titanium capsule 3. The implant 1 includes a detector stage 5, a pacemaker stage 7 capable of delivering stimulation pulses to the heart to treat both bradycardia and tachycardia, a mechanical defibrillation unit (a mechanical shock generator) 9, an electrical defibrillation unit 11, a control unit 13, a diagnostics unit 15 and a telemetry unit 17. The different stages and units in the implant 1 communicate internally with one other by means of a data bus 19.

The implant 1 communicates externally, i.e., to and from a programmer 21, via the telemetry unit 17. Such communications primarily include programming of the implant 1 and transmission of diagnostic data for different types of events, as well as sensor signals and ECG signals, from the diagnostic unit 15.

The implant 1 is connected to a heart 25 via a system of electrode conductors 23 in order to deliver both pacemaker pulses and shock pulses to the heart, and to receive signals therefrom, indicative of the condition of the heart. FIG. 1 is only a schematic, and signals indicative of the condition (electrical and/or mechanical activity) of the heart 25 also include signals from measurements of physiological variables, such as the partial pressure of oxygen (PO2) in the blood, from other sites in the body.

As described above, the defibrillation implant 1 includes the functions included in a modern defibrillator (AICD) of the initially described kind, in addition to the mechanical defibrillation stage 9, which is described in greater detail below. Thus, the detection stage 5 monitors the heart's condition by means, for example, of an IECG monitoring device 27 and a sensor signal monitoring device 29, in order to detect normal sinus rhythm or abnormal cardiac conditions requiring treatment, e.g., bradycardia, hemodynamically stable/unstable tachycardia and ventricular fibrillation.

Data from the detection stage 5 are sent to the control unit 13 which, on the basis of these data, orders the requisite therapy, such as tachycardia-terminating stimulation, and sends a command signal to at least one of the stages 7, 9, and 11, i.e., to the pacemaker stage 7 in the exemplified tachycardia-terminating stimulation.

The hitherto described parts and functions of the defibrillation implant 1 are, as noted above, conventional in nature, and will henceforth only be mentioned to the extent that they relate to the inventive mechanical defibrillator/cardioverter 9 (henceforth referred to as the mechanical defibrillator) which will now be described.

Figure 3:
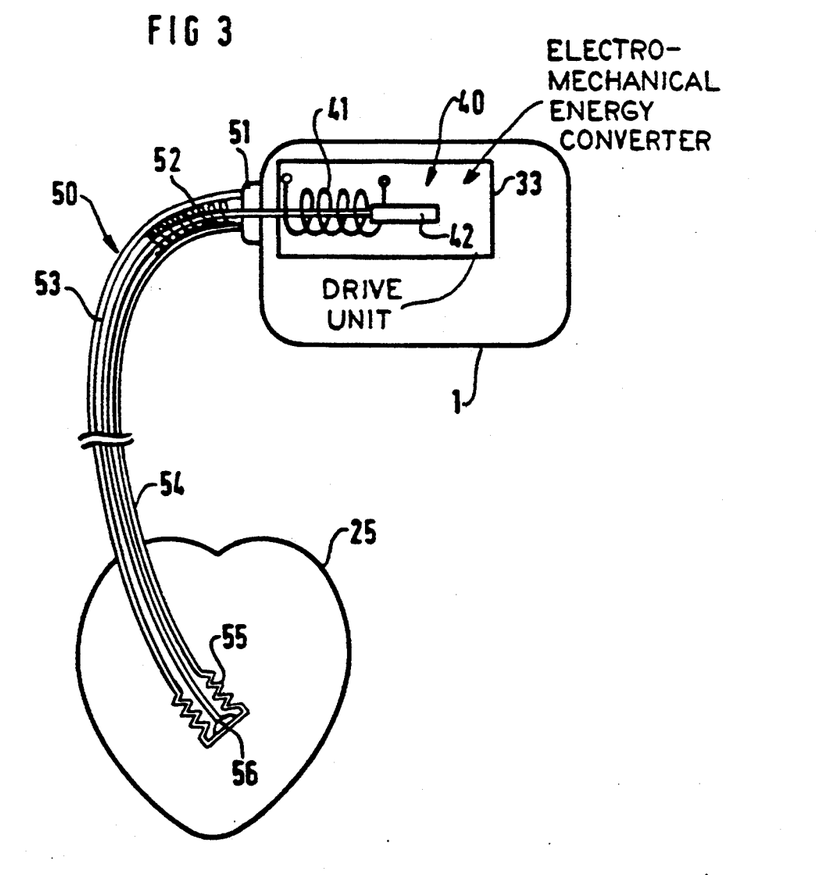
FIG. 3 is a schematic representation of a first embodiment of the electromechanical energy converter used in the invention, with an associated electrode.

The mechanical defibrillator 9 includes a time control unit 31 and a drive unit 33 for a mechanical electrode 50 (FIG. 3). The time control unit 31 makes a decision as to the pulses, pulse sequences and continuous output signals to be supplied by the mechanical defibrillator 9. The, drive unit 33 supplies the mechanical electrode 50 with sufficient energy to generate the desired mechanical defibrillation shocks.

Figure 2A:
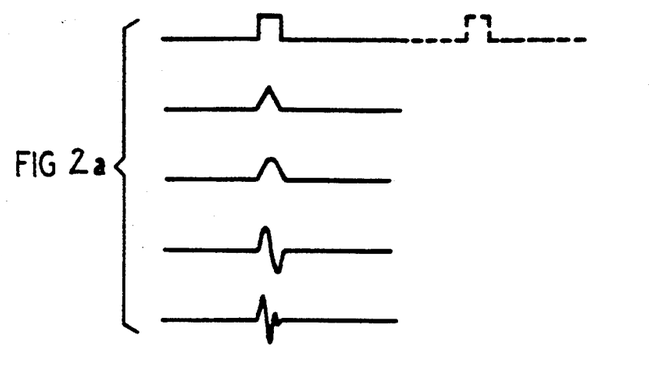
FIGS. 2a, 2b and 2c show illustrative examples of patterns for the mechanical defibrillation shock.
Figure 2B:
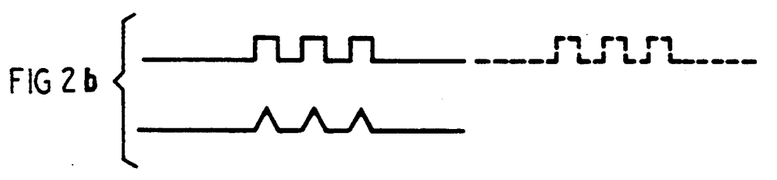
Figure 2C:
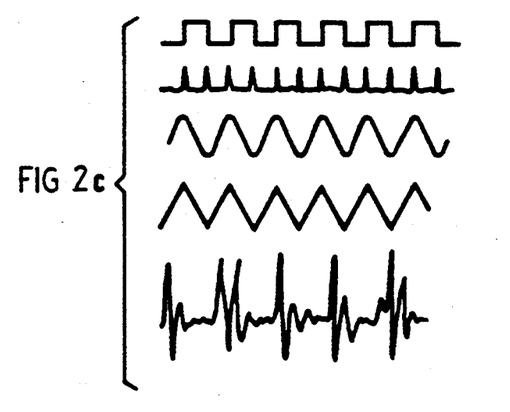

Examples of such shocks are shown in FIG. 2.

FIG. 2a shows examples of different morphologies for individual pulses. As indicated by the dashed line for the additional square wave, the pulses can be repeated if necessary.

FIG. 2b shows examples of pulse trains or pulse sequences composed of pulses of the kind shown in FIG. 2a, square and triangular pulses in this instance.

FIG. 2c shows examples of different continuous signals which can be supplied for mechanical defibrillation of the heart.

The drive unit 33 contains an electromechanical energy converter 40 of the kind shown in FIG. 3. The energy converter 40 has an electromagnetic coil 41, encompassing a moveable rod 42 made of a magnetic material, e.g. soft iron material or permanent magnet material. Any change in current through the coil 41 changes the coil's magnetic field, and thus the position of the rod 42 in relation to the coil 41.

The electromagnetic converter 40 is functionally closely related to an electrode 50 serving as a line for transmitting mechanical energy from the energy converter 40 to the heart 25.

The outer part of the electrode 50 is devised in the manner of a Bowden cable, with a wire 54 in its interior. The outer part of the electrode 50 is formed by a helix 52 made of, e.g., MP 35 provided with a protective sleeve 53 made of, e.g., silicone rubber or some other biocompatible polymer material. The wire 54, for transmission of the mechanical energy, can move in relation to the interior of the helix 52.

At the distal end of the electrode 50, the sleeve 53 is devised as an elastic, expandable bellows 55 which can also be made of silicone rubber. The bellows 55 prevents blood from penetrating into the electrode 50 during movements of the wire 54. Even if body fluid is thereby prevented from entering the electrode 50, a seal 51 is also provided between the defibrillator implant 1 and the electrode 50, since the electrode, owing to the permeability of the sleeve 53, is filled with a fluid, mainly consisting of deionized water, after implantation.

The wire 54 is attached, at its proximal end, to the rod 42, and, at its distal end, to a mechanical electrode head forming a pressure distribution plate 56 which presses against/is attached to the bellows 55.

The described design according to FIG. 3 achieves mechanical defibrillation of the heart 25 when the time control unit 31, responding to command signals from the control unit 13, orders the drive unit 33 to emit mechanical shocks of the kind shown in FIG. 2 to the heart 25. Changes in current through the coil 41 cause movement of the rod 42, which is transmitted by the wire 54 and causes a stroke-like movement of the bellows 55, thereby exerting a mechanical action on the heart 25.

The electromechanical conversion of energy can be achieved in some other way than the one described here, e.g. through utilization of the piezo effect or the electro/magnetostrictive effect. The transmission of power to the wire 54 can also be achieved in some other way than with the described rectilinear movement, e.g., by affixing the wire 54 to an arm, rotatable around a bearing point, which is acted on by the moving part in the energy converter.

The electrode 50 can be devised with a plurality of distal ends enabling the heart to be defibrillated at a plurality of different sites. The electrode 50 could be e.g. Y-shaped, the wire 54 being subdivided and devised accordingly.

Figure 4:
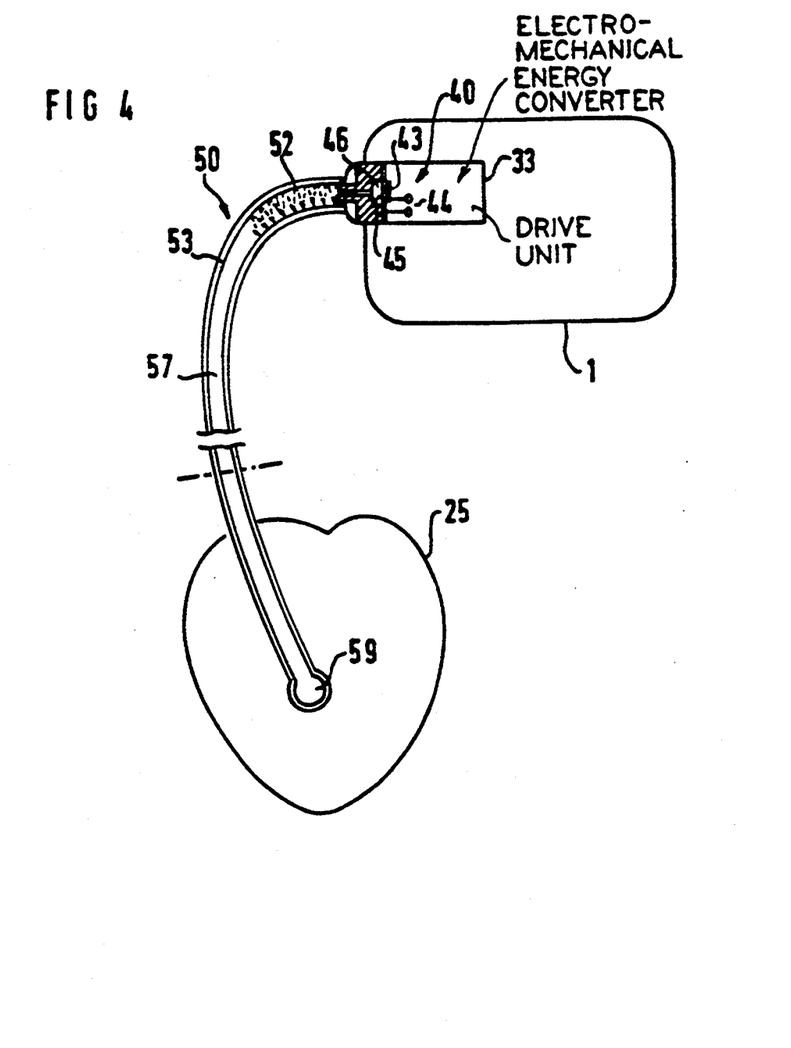
FIG. 4 is a schematic representation of a second embodiment of the electromechanical energy converter used in the invention, with an associated electrode.
Figure 5:
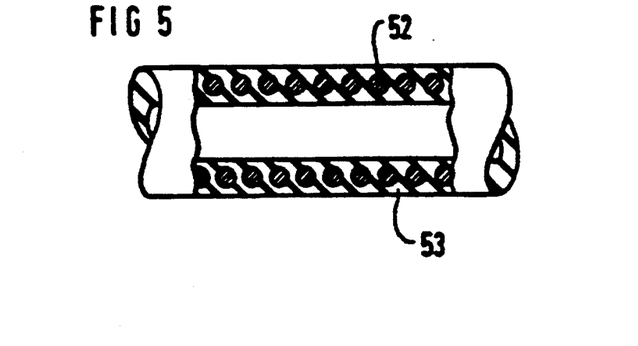
FIG. 5 shows a longitudinal cross-section through the electrode according to FIG. 4.

In FIGS. 4 and 5, an alternative embodiment is described for the electromechanical energy converter 40 and the electrode 50, which can also be provided with a plurality of distal ends. In this embodiment, pressure is generated in the energy converter 40 when a piezoelectric crystal 43 receives electrical energy via two electrode connectors 44 and converts the electrical energy into mechanical energy in a known way. The mechanical energy, via an elastic membrane 45, generates pressure in a pressure chamber 46. The pressure chamber 46, which is made of a material resistant to pressure deformation, is connected to an electrode 50 devised as a hydraulic line or hose. The electrode 50 has an outer part with a sleeve 53 and a helix 52, as described in conjunction with FIG. 3, although with the difference that the helix 52 is embedded as the core of the sleeve 53, as shown in FIG. 5, so the electrode 50 exhibits strong resistance to pressure. Inside the electrode 50 there is a fluid 57, mainly consisting of deionized water, as previously noted, which serves as a medium for transmitting the pressure generated in the pressure chamber 46. The fluid, which fills the electrode after implantation (any air which may be present diffuses out of the hose after a short time), is connected to one or a plurality of balloon-like sections 59 on the electrode, one such exemplifying section being shown at the distal end of the electrode in FIG. 4.

The described design according to FIGS. 4 and 5 achieves, as previously described, mechanical defibrillation of the heart 25 when the time control unit 31, according to command signals from the control unit 13, orders the drive unit 33 to emit mechanical shocks of the kind shown in FIG. 2 to the heart 25. The energy converter 40 achieves overpressure in the pressure chamber 46. This supplies pressure which, via the fluid 57, is transmitted to the balloon 59 so it expands in a stroke-like fashion and exerts a mechanical effect on the heart 25.

The energy converter 40 described in FIGS. 4 and 5 is, as noted in conjunction with FIG. 3, only one of a plurality of possible converters. Electrode placement can be varied, both in the design in FIG. 3 and the design in FIGS. 4 and 5, so that electrodes can be applied at e.g. an epicardiac site.

Another way of achieving the desired is to employ an electro-chemical energy converter 58 which utilizes two electrodes 44 placeable in the id 57. When a given electrical charge is passed through the fluid 57, the fluid disassociates, if it consists of deionized water, into hydrogen and oxygen. This gas mixture, when ignited with an electric spark also produced by the electrodes 44, produces a pressure wave in the fluid. The amount of gas generated in the fluid is strictly governed by the magnitude of the charge supplied, provided the fluid has poor conductivity, which is the case for deionized water. The pressure pulse, generated this way is extremely brief, distinct, and well-defined, making it suitable for generation of shock patterns shown in FIG. 2.

Another way of achieving the desired energy conversion entails utilization of the bubble jet art, known from ink jet printers, which can be summarized as follows. The ink in a printer contains a very small heatable plate which can be heated very rapidly (in times measured in $\mu s$) with a pulse of current, causing a gas bubble to form on the plate. The increase in volume achieved as a result of the bubble is utilized by the printer for ejecting a drop of ink. Ambient ink causes the gas bubble produced to cool and rapidly collapse. New pulses of current generate new gas bubbles at a rate sometimes exceeding 1 kHz.

Figure 7:
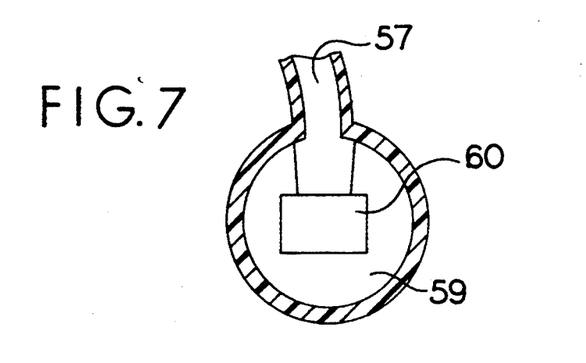
FIG. 7 is a sectional view of an embodiment of the invention employing a bubble jet generator.

When bubble, jet technology can be utilized in a mechanical defibrillator with a fluid-filled electrode 50 according to FIGS. 4 and 5, the heatable plate 60 can be placed either in the electrode 50 or in the drive unit 33. If placed in the electrode 50 in e.g. the balloon 59 as shown in FIG. 7, the balloon 59 expands when a pulse of current is applied causing gas to be generated, and a mechanical defibrillation pulse arises corresponding to the increase in pressure (the balloon then rapidly collapses). The leads to the plate 60, if disposed in the balloon 69, can be conducted as shown in FIG. 5. As previously noted, the pulses can be generated in succession as shown In FIG. 2

Figure 6:
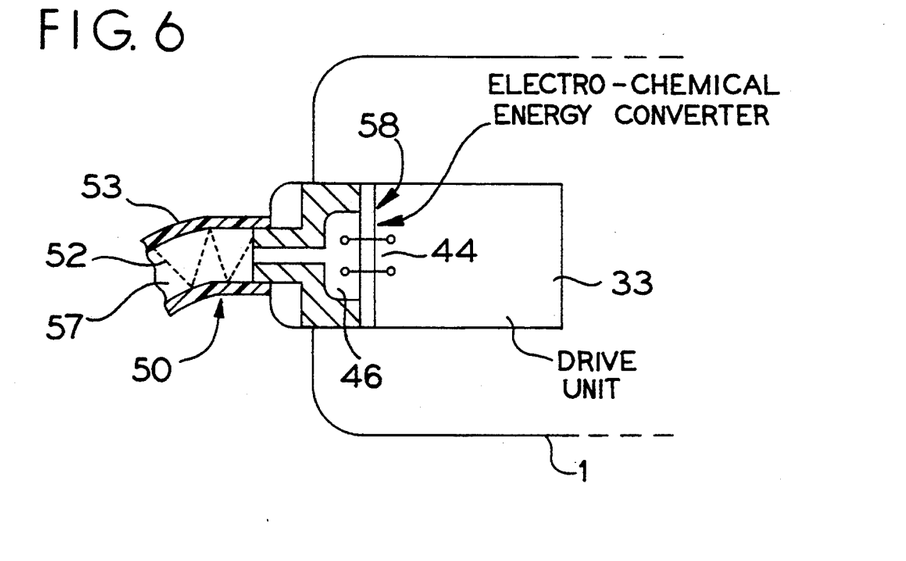
FIG. 6 is a schematic representation of a further embodiment of the invention, employing an electro-chemical energy converter.

If the heatable plate is placed in the drive unit 33, a transformation of energy takes place at that location, and the fluid 57 in the electrode 50 serves solely as a transmission medium for the pulse (s) as in the embodiment of FIG. 6.

Placement of the other energy converters 40, as shown in FIGS. 4 and 5 in the electrode 50, is also an alternative.

Figure 8:
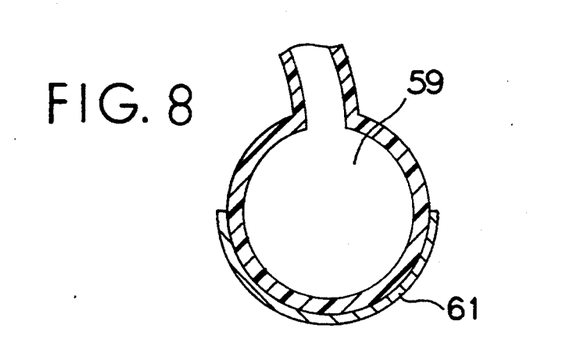
FIG. 8 is a sectional view through a further embodiment of the invention, employing an exterior element, which may be a magnetostrictive, electrostrictive of piezoelectric element.

The mechanical energy converter 40 can also operate by providing the electrode 50 with an element 61 on its distal exterior as shown in FIG. 8, which presses against heart tissue and converts the electrical energy into mechanical energy a known manner. This element 61 can, e.g., be a piezoelectric element in the form of a piezofilm or a ceramic piezoelement, or may be a magnetostrictive element or an electrostrictive element. The electrode (or electrodes) 50 can be devised for both intracardiac and epicardiac placement.

As noted initially, the implant 1 is capable in addition defibrillation by the mechanical defibrillator 9, of performing other electrical AICD functions. The mechanical defibrillator 9 is devised to collaborate via the control unit 13, with other AICD functions and to provide therapy corresponding to the detected condition of the heart.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable heart defibrillator comprising:
   implantable means for detecting a condition of a heart and for emitting a sensed condition signal;
   implantable control means for generating, dependent on said sensed condition signal, a command signal to initiate a selected cardiac therapy regimen including, when warranted by said sensed condition signal, a defibrillation regimen; and
   implantable shock generator means, responsive to said command signal, for generating at least one defibrillation shock pulse containing non-electrical energy as at least part of said defibrillation regimen; and including means adapted for contact with tissue of said heart for delivering said shock pulse containing said non-electrical energy to said heart as a direct mechanical impact to said heart tissue.

2. An implantable heart defibrillator as claimed in claim 1 wherein said means adapted for contact with tissue of said heart include electrode means for delivering said shock pulse containing said nonelectrical energy to said heart tissue.

3. An implantable heart defibrillator as claimed in claim 2 wherein said electrode means comprise a mechanical electrode having a distal end locatable at said heart with an electrode head disposed at said distal end which is mechanically movable in response to said non-electrical energy.

4. An implantable heart defibrillator as claimed in claim 1 wherein said shock pulse has a chronological morphology and wherein said shock generator means includes means for selectively configuring the chronological morphology of said shock pulse.

5. An implantable heart defibrillator as claimed in claim 1 wherein said shock generator means includes an electromechanical energy converter means for converting electrical energy into mechanical energy as said non-electrical energy.

6. An implantable heart defibrillator as claimed in claim 5 wherein said electromechanical energy converter means comprises at least one movable part, and means for producing a stroke motion by said movable part to produce said impact.

7. An implantable heart defibrillator as claimed in claim 6 wherein said shock generator means includes a mechanical electrode having an electrode head locatable at said heart for delivering said mechanical energy to said heart, said mechanical electrode including an outer electrode part and an inner electrode part, said inner electrode part comprising said movable part and being movable relative to said outer electrode part, said inner electrode part having a proximal end attached to said means for producing a stroke motion and a distal end attached to said electrode head, said means for producing a stroke motion causing said inner electrode part to move within said outer electrode part and thereby to impart said mechanical energy to said heart via said electrode head.

8. An implantable heart defibrillator as claimed in claim 7 wherein said outer electrode part comprises a sleeve and said inner electrode part comprises a wire slidable in said sleeve.

9. An implantable heart defibrillator as claimed in claim 7 wherein said electrode head comprises a bellows movable by said inner electrode part, and said bellows carrying a pressure distribution plate which interacts with said heart tissue to produce said impact.

10. An implantable heart defibrillator as claimed in claim 6 wherein said means for producing a stroke motion comprises means for electromagnetically producing a stroke motion to produce said impact.

11. An implantable heart defibrillator as claimed in claim 6 wherein said means for producing a stroke motion comprises means for piezoelectrically producing a stroke motion to produce said impact.

12. An implantable heart defibrillator as claimed in claim 1 wherein said means adapted for contact with tissue of said heart has an enclosure having an exterior adapted for contact with said heart and wherein said shock generator means includes electrochemical means for converting electrical energy into said mechanical energy by electrochemically generating pressure in said enclosure to produce said impact.

13. An implantable heart defibrillator as claimed in claim 12 wherein said shock generator means includes a mechanical electrode having an electrode head locatable at said heart for delivering said mechanical energy to said heart, said mechanical electrode including an outer electrode part and an inner electrode part, said inner electrode part containing a pressure-transfer medium in communication with said enclosure, said pressure-transfer medium transferring pressure from said enclosure to said distal end for delivery to said heart as said impact.

14. An implantable heart defibrillator as claimed in claim 13 wherein said pressure-transfer medium comprises a fluid, and wherein said electrode head comprises at least one elastic, expandable section at said distal end of said electrode.

15. An implantable heart defibrillator as claimed in claim 1 wherein said electrode means adapted for contact with tissue of said heart includes an electrode having an electrode head disposed at a distal end of said electrode locatable at said heart for delivering said mechanical energy to said heart, and electromechanical energy converter means disposed at said electrode head for converting electrical energy into said mechanical energy to produce said impact.

16. An implantable heart defibrillator as claimed in claim 15 wherein said electromechanical energy converter means comprise a piezoelectric element.

17. An implantable heart defibrillator as claimed in claim 15 wherein said electromechanical energy converter means comprises an electrostrictive element.

18. An implantable heart defibrillator as claimed in claim 15 wherein said electromechanical energy converter means comprises a magnetostrictive element.

19. An implantable heart defibrillator as claimed in claim 16 wherein said electromechanical energy converter means comprises a bubble jet generator.

20. An implantable heart defibrillator as claimed in claim 15 wherein said electromechanical energy converter means is disposed on an exterior of said electrode head.

21. An implantable heart defibrillator as claimed in claim 20 wherein said electromechanical energy converter means comprises a piezoelectric element.

22. An implantable heart defibrillator as claimed in claim 1 wherein said means adapted for contact with tissue of said heart comprises an electrode system having a plurality of energy delivery locations locatable at a plurality of respectively different locations at said heart for delivering said non-electrical energy as impacts to said heart at said plurality of different locations.

23. An implantable heart defibrillator as claimed in claim 1 further comprising means for delivering electrical stimulation to said heart, and wherein said control means comprises means for delivering a command signal to each of said shock generator means and said means for delivering electrical stimulation for shocking said heart with a combination of electrical energy from said means for delivering electrical stimulation and said nonelectrical energy from said shock generator means.

24. A method for defibrillating a heart comprising the steps of:
converting electrical energy into a non-electrical energy shock pulse; and
delivering said non-electrical energy shock pulse in vivo to a heart exhibiting fibrillation as a direct mechanical impact to tissue of said heart for defibrillating said heart.

25. A method for defibrillating a heart as claimed in claim 24 wherein the step of converting electrical energy into non-electrical energy is further defined by converting electrical energy into mechanical energy.

26. A method for defibrillating a heart as claimed in claim 25 wherein the step of converting electrical energy into mechanical energy is further defined by electromagnetically converting said electrical energy into said mechanical energy.

27. A method for defibrillating a heart as claimed in claim 25 wherein the step of converting electrical energy into mechanical energy is further defined by electrochemically converting said electrical energy into said mechanical energy.

28. A method for defibrillating a heart as claimed in claim 25 wherein the step of converting electrical energy into mechanical energy is further defined by piezoelectrically converting said electrical energy into said mechanical energy.

29. A method for defibrillating a heart as claimed in claim 25 wherein the step of converting electrical energy into mechanical energy is further defined by electrostrictively converting said electrical energy into said mechanical energy.

30. A method for defibrillating a heart as claimed in claim 25 wherein the step of converting electrical energy into mechanical energy is further defined by magnetostrictively converting said electrical energy into said mechanical energy.

31. A method for defibrillating a heart as claimed in claim 24 wherein the step of delivering said non-electrical energy in vivo to said heart is further defined by delivering said non-electrical energy in vivo to a plurality of locations at said heart.

32. An implantable heart defibrillator comprising:
implantable means for detecting a condition of a heart and for emitting a sensed condition signal;
implantable control means for generating, dependent on said sensed condition signal, a command signal to initiate a selected cardiac therapy regimen including, when warranted by said sensed condition signal, a defibrillation regimen; and
implantable shock generator means, responsive to said command signal, for generating at least one defibrillation shock by piezoelectrically converting electrical energy into mechanical energy, as at least part of said defibrillation regimen, and for delivering said shock containing said mechanical energy to said heart.

33. An implantable heart defibrillator comprising:
implantable means for detecting a condition of a heart and for emitting a sensed condition signal;
implantable control means for generating, dependent on said sensed condition signal, a command signal to initiate a selected cardiac therapy regimen including, when warranted by said sensed condition signal, a defibrillation regimen; and
implantable shock generator means, responsive to said command signal, for generating at least one defibrillation shock by converting electrical energy into chemical energy and converting said chemical energy into mechanical energy, as at least part of said defibrillation regimen, and for delivering said shock containing said mechanical energy to said heart.

34. An implantable heart defibrillator comprising:
implantable means for detecting a condition of a heart and for emitting a sensed condition signal;
implantable control means for generating, dependent on said sensed condition signal, a command signal to initiate a selected cardiac therapy regimen including, when warranted by said sensed condition signal, a defibrillation regimen; and
implantable bubble generator means, responsive to said command signal, for generating at least one defibrillation shock containing mechanical energy as at least part of said defibrillation regimen, and for delivering said shock containing said mechanical energy to said heart.

* * * * *